(12) United States Patent
Xia et al.

(10) Patent No.: US 8,222,046 B2
(45) Date of Patent: Jul. 17, 2012

(54) AMPLIFICATION FOR SOLID PHASE IMMUNOASSAY

(75) Inventors: Zong-Li Xia, Sunnyvale, CA (US); Raymond Chan, Redwood City, CA (US); Kelly Doan, San Jose, CA (US)

(73) Assignee: Remel, Inc., Lenexa, KS (US)

( * ) Notice: Subject to any disclaimer, the term of this patent is extended or adjusted under 35 U.S.C. 154(b) by 549 days.

(21) Appl. No.: 12/432,307

(22) Filed: Apr. 29, 2009

(65) Prior Publication Data

US 2010/0081125 A1 Apr. 1, 2010

Related U.S. Application Data

(62) Division of application No. 11/211,292, filed on Aug. 25, 2005, now abandoned.

(60) Provisional application No. 60/604,378, filed on Aug. 25, 2004.

(51) Int. Cl.
*G01N 33/558* (2006.01)

(52) U.S. Cl. ........ 436/514; 422/401; 422/420; 422/430; 435/7.5; 435/287.2; 435/287.7; 435/287.9; 435/805; 435/810; 435/970; 436/524; 436/527; 436/810

(58) Field of Classification Search .................. None
See application file for complete search history.

(56) References Cited

U.S. PATENT DOCUMENTS

| | | | |
|---|---|---|---|
| 4,094,647 A | 6/1978 | Deutsch et al. | |
| 4,235,601 A | 11/1980 | Deutsch et al. | |
| 4,361,537 A | 11/1982 | Deutsch et al. | |
| 4,656,143 A * | 4/1987 | Baker et al. | 436/527 |
| 4,737,453 A * | 4/1988 | Primus | 435/5 |
| 4,959,307 A | 9/1990 | Olson | |
| 5,120,643 A | 6/1992 | Ching et al. | |
| 5,141,850 A | 8/1992 | Cole et al. | |
| 5,212,063 A | 5/1993 | Ofenloch-Hahnle et al. | |
| 5,268,306 A | 12/1993 | Berger et al. | |
| 5,543,332 A | 8/1996 | Lihme et al. | |
| 5,602,040 A | 2/1997 | May et al. | |
| 5,714,389 A | 2/1998 | Charlton et al. | |
| 6,352,862 B1 | 3/2002 | Davies et al. | |
| 6,703,196 B1 * | 3/2004 | Klepp et al. | 435/4 |
| 6,790,611 B2 | 9/2004 | Lassen et al. | |

OTHER PUBLICATIONS

Cazacu et al., Comparison of a New Lateral-Flow Chromatographic Membrane Immunoassay to Viral Culture for Rapid Detection and Differentiation of Influenza A and B Viruses in Respiratory Specimens, Journal of Clinical Microbiology, 2004, 42:3661-3664.
Remel/Apogent, X/pect™ Flu A&B, Product Insert, Remel Inc., IFU 24600, Revised Aug. 28, 2003, 4 pages.

* cited by examiner

*Primary Examiner* — Chris L Chin
(74) *Attorney, Agent, or Firm* — Thompson Hine LLP

(57) ABSTRACT

The present invention is directed to immunoassays for detecting one or more target analytes in a fluid sample wherein the detection reaction occurs on a solid support and involves an amplification system. In particular, the invention is directed to making and using a test device having at least one site for detecting the presence of at least one target analyte, wherein a conjugate comprising dextran-polystreptavidin is immobilized at the test site(s) as a capture reagent for a complex containing the target analyze.

8 Claims, 1 Drawing Sheet

AMPLIFICATION FOR SOLID PHASE IMMUNOASSAY

CROSS REFERENCE TO RELATED APPLICATION

The present application is a Division of U.S. application Ser. No. 11/221,292, filed Aug. 25, 2005, now abandoned which claims priority from U.S. Provisional Patent Application Ser. No. 60/604,378 filed on Aug. 25, 2004, both of which are expressly incorporated by reference herein.

FIELD OF THE INVENTION

The present invention is directed to immunoassays for detecting one or more target analytes in a fluid sample wherein the detection reaction occurs on a solid support.

BACKGROUND OF THE INVENTION

Immunoassays have become methods of choice for rapid in vitro diagnostics due in part to the ease of use, speed of reaction, and relatively low cost. A common immunoassay format comprises a "capture" reagent immobilized on a solid substrate wherein the capture reagent is capable of binding the target analyte, or a complex containing the target analyte, or a molecule that competes with the target analyte for binding sites on the capture reagent. By localizing the capture reagent in a restricted zone or area, the result of the immunoassay is readily visualized or detected.

In particular, immunoassays in the form of lateral flow test strips for the rapid analysis of fluids, including, but not limited to, body fluids such as urine, saliva, serum, plasma, whole blood, spinal fluid, amniotic fluid, and the like, or liquid extracts of specimens such as feces, sputum, nasal swabs, etc., are popular as a means of determining the presence or absence of target analytes, such as hormones, drugs, allergens, and disease-related antigens. Examples of lateral flow devices are disclosed in U.S. Pat. Nos. 4,094,647, 4,235,601, and 4,361,537 to Deutsch et al., as well as U.S. Pat. No. 5,120,643 to Ching et al., U.S. Pat. No. 5,602,040 to May et al., U.S. Pat. No. 5,714,389 to Charlton et al., and U.S. Pat. No. 6,352,862 to Davis et al., among many others.

Regarding ease of use, typically very little, if any, specimen processing is required prior to adding a liquid sample to a test strip. Therefore, preferably, the sensitivity of a lateral flow test device is adequate to detect or measure a minimal biologically and/or physiologically significant concentration of particular target analyte, as may be expected to be contained within a fluid specimen as collected, without requiring additional processing to concentrate the target analyte prior to testing. Such restrictions on processing present a challenge when the biologically or physiologically meaningful concentration of a target analyte is low. Also, throat or nasal swabs, sputum, semen, vaginal and cervical secretions and other sorts of viscous specimens usually require addition of a reagent to extract, breakdown or "thin" the sample to achieve an appropriately liquid state to flow through a test device. Addition of such reagents leads to further dilution of the concentration of target analytes, compounding the problem of detecting low levels of target analytes that may be present in a mucus specimen, throat swab, semen, and the like.

Methods of increasing the amount of detectable label captured at a test site have been described. U.S. Pat. No. 5,141,850 to Cole et al., expressly incorporated by reference herein in its entirety, teaches the binding of a "capturable" reagent to the target analyte, along with binding of a labeled reagent, and the immobilization of a capture reagent specific for the capturable component. A preferred embodiment uses streptavidin conjugated to latex particles and localized within the pores of the porous carrier material at the test site by depositing the particles under mild vacuum conditions. However, conjugation of streptavidin to latex particles adds to the labor and cost of manufacturing the test device and entrapping particles within the pores of the carrier material is not equivalent to chemically or physically binding, directly or indirectly, the capture reagent to the carrier material. Moreover, entrapment of latex particles within a carrier material requires porosity sufficient to contain particles, but is not desirable for use in connection with samples containing cellular contaminants and/or debris, such as sputum samples, semen, vagina and cervical secretions, whole blood, and the like.

Another approach to amplification of detection within an immunoassay is to use polymeric carriers in preparing various conjugated reagents. Such polymeric conjugates are disclosed in U.S. Pat. No. 5,543,332 to Lihme et al. (expressly incorporated by reference herein in its entirety). One example is a dextran-polystreptavidin conjugate. Conjugation of multiple molecules of streptavidin to each dextran molecule significantly increases the number of available streptavidin molecules within a localized area for binding to a receptor molecule, namely biotin, thereby amplifying the amount of biotinylated molecules captured within a localized area.

It is known to use dextran-polystreptavidin for preparing conjugate reagents that react in a "free" form (not immobilized on a solid support) in solution, for binding to or competing with a target analyte. Such reagents are taught in U.S. Pat. No. 5,543,332 in connection with ELISA and "dot-blot" immunoassays wherein biotin is immobilized on a solid support and, thus, biotin serves as the capture reagent. More recently, polymeric conjugates are described in U.S. Pat. No. 6,709,611 to Lassen et al. in connection with an assay for detecting respiratory syncytial virus (RSV), wherein a dextran polymeric carrier is used as a "mobile solid phase", for example, to prepare labeling reagents.

SUMMARY OF THE INVENTION

The present invention is directed to immunoassays incorporating an amplification system. In particular, the invention is directed to making and using a test device having at least one site for detecting the presence of at least one target analyte, wherein a conjugate comprising dextran-polystreptavidin is immobilized at the test site(s) as a capture reagent. Applicants discovered that dextran-polystreptavidin can be immobilized on a porous carrier material, such as nitrocellulose, by altering the "curing" conditions compared to those typically used to immobilize antibodies, antigens, or other proteins that comprise standard capture reagents. The immobilized dextran-polystreptavidin substantially remains as a discrete band.

Streptavidin moieties within the immobilized dextran-polystreptavidin conjugate bind specifically to biotin; thus a biotinylated component, such as a biotinylated binding partner to the analyte, is used. For example, biotinylated antibodies specific for a target analyte can be utilized, or if the target analyte is itself an antibody, then a biotinylated antigen can be used. Likewise, hormones, receptors, and the like can serve as target analytes, and appropriate ligands that specifically bind to the hormones, receptors, or other target analyte are conjugated to biotin. In one embodiment, biotinylated conjugates are dried or lyophilized in a separate area from other dried components, such as dried labeled conjugates, because separating the biotinylated conjugate in a separate site from the site containing a labeled conjugate appears to further improve the sensitivity of the device using dextran-polystreptavidin as a capture component. In one embodiment, the biotinylated conjugate, such as a biotinylated antibody or antibody fragment capable of specifically binding to a target analyte, is placed upstream of the labeled component, which is, in turn, upstream from the test site(s).

In one embodiment, a biotinylated antibody capable of specifically binding the target analyte is dried within a piece of porous plastic, such as product #4588 from Porex (Fairburn, Ga.). The labeled component, for example, another antibody capable of binding the target analyte conjugated to a detectable label, including but not limited to an enzyme or enzyme fragment, metal sol, latex particle, fluorescent molecules or dye, is dried within a glass fiber pad, for example, glass fiber #66078 from Gelman Sciences (Ann Arbor, Mich.), downstream from the biotinylated conjugate. Continuing downstream, the dextran-polystreptavidin capture component, such as product #OA222 commercially available from DakoCytomation (Carpinteria, Calif.), is dried on a porous material, such as Millipore HiFlow Plus HF13502 or HF12002 (Millipore, Billerica, Mass.), although other porous chromatographic materials, such as those made from nitrocellulose, paper, or nylon may be used.

DETAILED DESCRIPTION OF THE INVENTION

Figure 1:
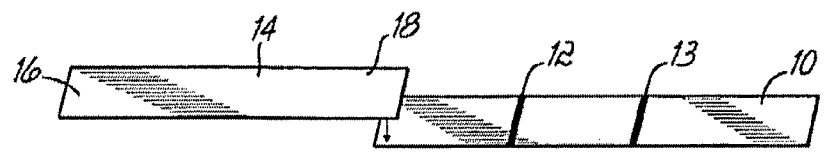
FIG. 1 shows an expanded perspective of one embodiment of a test strip for performing a lateral flow immunoassay comprising two separate porous carrier materials.

FIG. 1 shows one embodiment of the invention in a lateral flow format. A first porous material 10, such as nitrocellulose or other suitable porous substrate known in the art, contains at least one test site 12 comprising immobilized dextran-polystreptavidin, for example, product #OA222 commercially available from DakoCytomation (Carpinteria, Calif.). Upstream of the first porous material 10 is a second porous material 14 that serves as the sample application site 16 and as the conjugate site 18 containing dried biotinylated antibodies capable of specifically binding a target analyte and also containing antibodies conjugated to a detectable moiety (label) and capable of specifically binding a target analyte. In one embodiment, the second porous material 14 overlaps the first porous material 10 or otherwise forms contact that permits lateral flow of the fluid specimen from the first porous material 10 into the second porous material 14. An optional control site 13 is located on the first porous material 10 downstream of the test site(s) 12. The porous material may be beaded agarose, beaded polyacrylamide, porous glass, cellulose or other materials permeable to liquid and compatible with the assay components and test analyte.

Figure 2:
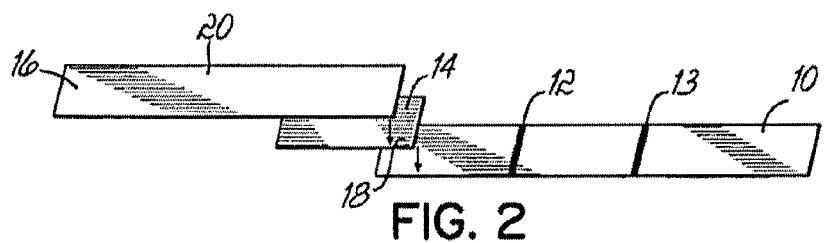
FIG. 2 is an expanded perspective of another embodiment of a test strip for performing a lateral flow immunoassay comprising three separate components.

FIG. 2 shows another embodiment of the invention wherein the sample application site 16 is contained in a third porous material serving as a receiving area 20 separate from the conjugate site 18. Such systems are known in the art. In one embodiment, the material forming the receiving area 20 overlaps the second porous material 14 containing the conjugate site 18 or otherwise forms contact that permits lateral flow of the fluid specimen.

Figure 3:
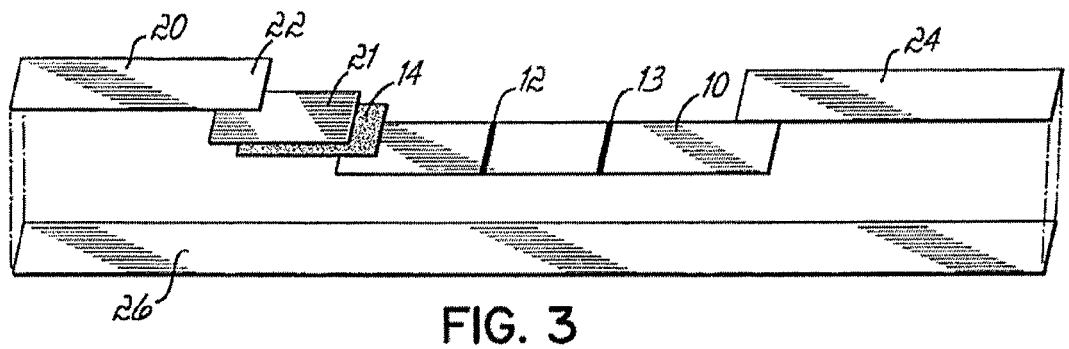
FIG. 3 illustrates an expanded perspective of a composite test strip comprising five components and a backing support material.

Yet another embodiment of the invention is shown in FIG. 3. The third porous material serving as the receiving area 20 further contains a dried biotinylated conjugate and is referred to as the biotinylated conjugate pad 22. The biotinylated conjugate pad 22 is shown upstream of, and in fluid contact with, a second porous material 14 containing the dried labeled conjugate, but the order may be reversed so that the biotinylated conjugate is downstream from the labeled conjugate. Further downstream from both conjugates, is the first porous material 10 containing at least one test site 12 comprising immobilized dextran-polystreptavidin conjugate.

As further shown in FIG. 3, with certain types of specimens, additional filtering is beneficial to reduce streaking and other background problems that may interfere with interpretation of test results. Additional filtering is provided by including a blank piece 21 of porous material, such as a piece of glass fiber, between the biotinylated conjugate pad 22 and the first porous material 10 which, in one embodiment, is directly between the biotinylated conjugate pad 22 and the second porous material 14 containing the dried labeled conjugate.

In one embodiment, the device also includes an absorbent pad 24 at the distal end of the first porous material 10 to function as a "sink" for the fluid specimen and facilitate adequate capillary flow through the test device. The absorbent pad 24 is comprised of paper, such as D28 from Whatman (Fairfield, N.J.) or other suitable absorbent material such as cotton, cellulose and other materials as known in the art. In one embodiment, all components are held in place via a backing support 26, such as vinyl with adhesive on one side, to maintain appropriate functional relationships and ensure proper performance.

As a specific example of one embodiment, a lateral flow test device for detecting influenza A and influenza B antigens is described in detail in the examples below.

Example 1

Biotinylated Antibodies

An antibody specific to influenza A antigens, for example monoclonal antibody product #1G4 from Diagnostic Products Corporation (DPC; Los Angeles Calif.) and an antibody specific to influenza B antigens, such as monoclonal antibody product #B35G (DakoCytomation, Carpinteria Calif.) and/or monoclonal antibody product 8F10E10 (Argene Inc., North Massapequa N.Y.), were separately coupled to biotin (for example, Sulfo-NHS-LC biotin, Pierce Biotechnology, Inc., Rockford Ill.) by methods known in the art. In one embodiment, coupling was done at a concentration of 2 mg of antibody per ml and the final conjugated product was diluted approximately 1:75 for use in making the test device.

In one embodiment, biotinylated antibodies were vacuum dried by methods known in the art within a piece of porous plastic, for example, Porex #4588, which is cut into strips for the test device. However, other porous material, such as glass fiber, can be used. In one embodiment, the biotinylated antibodies were dried into separate pieces of porous material. In another embodiment, the biotinylated antibodies for influenza A and for influenza B were dried within the same porous material. The dried antibodies must be capable of becoming rehydrated and soluble in the liquid specimen as it moves through the device.

Example 2

Labeled Antibodies

Antibodies specific for influenza A antigens and antibodies specific for influenza B antigens were conjugated with detectable labeling moieties. Either distinguishable labels or the same label can be used to label each different antibody. Suitable labels include, but are not limited to, metal sols, latex particles, enzymes, fluorescent molecules, and the like, as known in the art. One label is carboxylate-modified latex particles (Seradyn, Indianapolis Ind.) available in various colors. Antibodies were coupled to carboxylate-modified latex particles using carbodiimide N-hydroxysuccinimide linkage, by standard procedures known in the art. Separate monoclonal antibody products from those used to prepare biotinylated reagents can be used, if available, or the same antibody product can be used for biotin-conjugation and for conjugation with a labeling moiety.

The labeled antibodies were vacuum dried by methods known in the art within a porous material, such as glass fiber, and the porous material was cut into sections for use in a test device. The labeled antibodies can be dried together or each can be dried in separate pieces of porous material. The labeled antibodies must be capable of being rehydrated and soluble in the liquid specimen as it moves through the device.

Example 3

Test Strip with Test Site and Optional Control Site

Dextran-polystreptavidin was immobilized as a capture reagent at a test site on a porous material. In one embodiment, the porous material was nitrocellulose, such as Millipore HiFlow Plus HF12002 or HF13502 (Millipore, Billerica Mass.). Dextran-polystreptavidin reagent was mixed in phosphate buffed saline (PBS) supplemented with sucrose (approximately 2.5%) and EDTA (approximately 0.33 mM), and deposited in one or more discrete bands or zones on the porous material, and allowed to dry or "cure" for about 10 to 15 hours at 60° C. or about 7 to 14 days at room temperature. Although these time and temperature conditions were sufficient to immobilize the dextran-polystreptavidin conjugate on the porous material, they are exemplary and the invention is not limited to these specific conditions, but includes other conditions that result in immobilization.

A simple method for checking the quality of immobilization was to add a fluorescent molecule, such as fluorescein, to the PBS striping solution containing the dextran-polystreptavidin conjugate. After the striping process and curing period, a sample test strip was wetted at one end to permit an aqueous solution to flow laterally through the test site and the integrity of the striped band was checked or monitored by observation under ultraviolet light to ensure the test band remained discrete. Such methods are known and have become standard in the art.

To serve as a control site, antibodies specific to mouse IgG, such as goat-anti-mouse or rabbit-anti-mouse antiserum, were deposited at a discrete band or zone on the porous material and allowed to dry at 60° C. for about 45 minutes to about one hour or at room temperature for about 10-15 hours.

Example 4

Assembling the Composite Strip

As shown in FIG. 3, various components comprising the composite strip were anchored or secured on a backing support 26, such as an adhesive backing material, for example, white vinyl having a thickness of about 0.001 inches to about 0.03 inches. Such material is available from numerous sources. The first porous material 10 of the composite test strip, containing at least one test site 12, and optionally containing a control site 13, was positioned downstream of a conjugate pad 14 containing the labeled conjugate. The labeled conjugate pad 14 must overlap or make contact with the test strip 10 such that fluid possibly containing a target analyte moves laterally through the labeled conjugate pad 14 and through the test site 12. The use of an absorbent material 24 at the far downstream end of the first porous material 10 facilitated wicking or capillary flow through the test site 12 and acted as a sink to contain the fluid sample. Optionally, a blank filter 21 (free from immunoreactive reagents) was placed between the biotinylated conjugate pad 22 and the second porous material 14 containing the labeled conjugate to reduce streaking and other background problems that are associated with specimens containing high levels of cellular components and debris.

Example 5

Device for Detecting Influenza A and B Antigens

Figure 4:
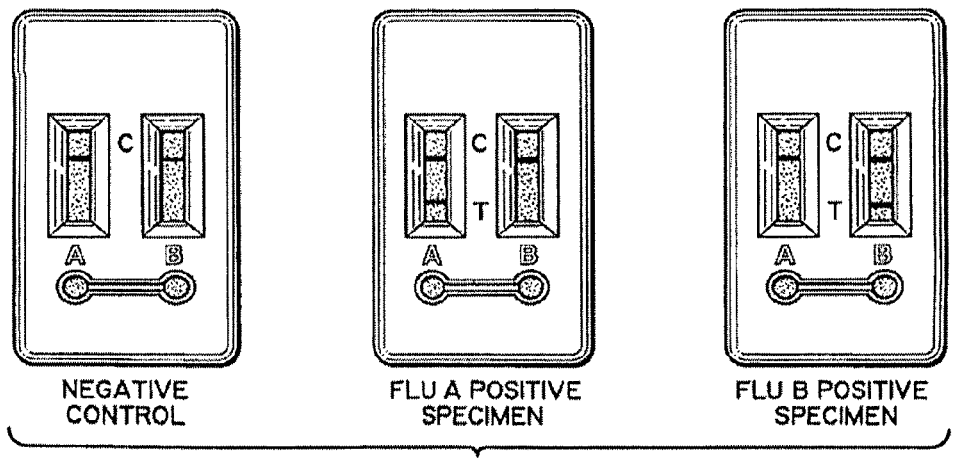
FIG. 4 shows a housing containing two separate test strips for two different antigens.

FIG. 4 illustrates a single device to detect two or more different target analytes, such as influenza antigens A and B, containing two separate composite test strips housed within a single housing or cassette 28. Each test strip has a test site 12 comprising immobilized dextran-polystreptavidin and a control site 13 with immobilized anti-mouse IgG antibodies although other capture reagent suitable for control purposes may be used. It will be appreciated that the two separate composite test strips may detect the same analytes.

Each of the test devices within the cassette 28 comprised the composite carrier membrane shown in expanded perspective in FIG. 3. In one embodiment, separate biotinylated conjugate pads 22 were used, upstream of the labeled conjugate pad 14, with one comprising dried biotinylated antibodies directed against influenza A antigens, and the other comprising dried biotinylated antibodies to influenza B antigens. In one embodiment, a blank piece 21 of glass fiber or other filtering material was placed directly between each biotinylated conjugate pad 22 and adjacent labeled conjugate pad 14.

Example 6

Using a Test Device to Detect Influenza A and/or B Antigens

Acceptable specimens for use with an influenza test device included nasal washes, nasal swabs, throat swabs, sputum and the like. Samples could be tested immediately upon collection or, alternatively, samples could be stored in suitable transport and storage medium, for example M4® (Remel, Lenexa Kans.) at 2-8° C. for up to about 72 hours prior to testing.

Freshly collected specimens could be tested immediately without the use of transport medium. Alternatively, specimens could be placed into a suitable transport medium, maintained at 2-8° C. and tested within 72 hours after collection. Frozen specimens in a suitable liquid viral transport medium stored at −20° C. or below in a non-defrosting freezer could be tested up to six months after collection. Multiple freeze-thaw cycles should be avoided.

The following transport media have been evaluated and found to be compatible: Amies Medium; Bartels Vital Transport Medium; Cary Blair Medium; Earle's Minimum Essential Medium (EMEM); EMEM with 1% Bovine Serum Albumin; EMEM with 1% Lactalbumin hydrolysate; Hank's Balanced Salt Solution; Liquid Stuarts Medium; M4™; M4-RT™; M5™; Phosphate Buffered Saline (PBS); PBS with 0.5% Bovine Serum Albumin; PBS with 0.5% Gelatin; Saline (normal); Sucrose Phosphate; Tryptic Soy Broth with 0.5% Bovine Serum Albumin; Tryptic Soy Broth with 0.5% gelatin; Veal Infusion Broth; and Veal Infusion Broth with 0.5% Bovine Serum Albumin.

A foil pouch may contain one single-use test device with two membrane strips. In one embodiment, the strips in the device contain, respectively, antibodies to influenza A or B. A specimen diluent may be included; the specimen diluent may be a buffered saline solution with detergent, a mucolytic agent, and preservative. In one embodiment, flexible plastic tubes for specimen preparation and disposable transfer pipettes are included; the pipettes with marked gradations at approximately 0.1 ml increments. A Flu A+/B− control swab, which is a dry swab containing inactivated influenza A antigen, and a Flu B+/A− control swab, which is a dry swab containing inactivated influenza B antigen, may be included.

The test device is removed from the foil pouch when the assay is to be performed. It is placed on a flat surface. If the kit and/or components have been refrigerated, they are allowed to equilibrate to room temperature.

For swab specimens without dilution (swab not submerged in a sufficient volume of transport media to allow processing of 0.1 ml) in transport media (including quality control swabs provided with the kit), 25 drops (approximately 0.6 ml) of specimen diluent are dispensed into a dilution tube. The swab specimen is placed in the tube and the tube is mixed thoroughly or vortexed to release bound antigenic material from the swab. The swab is rotated firmly against the tube walls then squeezed against the sides of the tube during removal.

For all specimens except swab specimens without transport media, 5 drops (approximately 0.1 ml) of specimen diluent is dispensed into the dilution tube. The specimens are mixed well and 0.1 ml (first molded graduated mark from the tip of transfer pipette) of liquid specimen (nasal wash or specimens in transport medium) is transferred into a dilution tube.

Using a transfer pipette, 0.2 ml (second graduated mark from tip of pipette) of specimen is dispensed into the center of the sample well of the test device. Test results are visually read after 15 minutes or up to 30 minutes as will be subsequently described. A strong positive result may be apparent sooner than 15 minutes.

Specimens, if needed, are exposed to a suitable extraction solution. For example, an aqueous solution comprising about 3% bovine serum albumin, about 3% non-ionic detergent, 0.1% casein, 0.1% N-acetyl-cysteine, 0.5 M sodium chloride, 25 mM monobasic sodium phosphate, 75 mM dibasic sodium phosphate, 0.05% Proclin 300, adjusted to a pH of about 7.4, is an effective extraction solution. For fresh swab specimens (not in a transport medium), the swab is placed into approximately 0.6 ml of extraction solution in a flexible plastic tube. The specimen is mixed, preferably via vortexing, to release bound potentially antigenic material, and the swab is squeezed by compressing the walls of the flexible tube while removing the swab. For liquid specimens, including nasal washes or transport media exposed to swab specimens, about 0.1 ml of extraction solution is mixed with about 0.1 ml of specimen.

About 0.20 to 0.25 ml of the extract is transferred to the sample application area of the test device. The liquid specimen moves laterally via wicking or capillarity through the device, rehydrating the dried biotinylated conjugates and the dried labeled conjugates. If the target analyte is present, it becomes sandwiched between the biotin-conjugate and the labeled conjugate. The streptavidin moieties of the dextran-polystreptavidin capture component bind the biotinylated conjugate regardless of whether the biotinylated conjugate is also bound to target analyte. However, if complexes of the biotinylated antibodies, target analyte and, hence, the labeled conjugate have formed, the labeled conjugate will form a detectable region at the capture site as the biotinylated conjugate is captured by immobilized streptavidin moieties. Optionally, excess unbound labeled conjugate is captured at a control site downstream of the test site(s).

Test results are interpreted as follows. The test device has two separate read windows; the one on the left for Flu A and the one on the right for Flu B as depicted in FIG. 4. A positive test, indicating that antigen is present in the specimen, is indicated by two black-colored bands; one in the test (T) region and one in the control (C) region. A negative test, indicating that antigen was not detected, is indicated by only one black-colored band in the control (C) region. An invalid test results in no black-colored band in the control (C) region. A complete, black, clearly visible test line of any intensity should be interpreted as positive. Invalid results due to excessively mucoid specimens may be repeated using twice the normal volume of specimen diluent during the dilution step.

Results may be reported as follows: positive for influenza A and/or influenza B antigen; negative for influenza A and/or influenza B antigen; or infection due to influenza A or B cannot be ruled out since the antigen present in the specimen may be below the detection limit of the test. Specimens in which a negative result was obtained should be cultured for confirmation.

For internal quality control, a procedural control may be included in the test. A colored band appearing on the control band (C) region is considered an internal positive procedural control, indicating proper performance and reactive reagents. A clear background in the results area is considered an internal negative control. If the test has been performed correctly and reagents are working properly, the background will clear to give a discernible result.

For external quality control, positive and negative controls should be assayed with each new test kit lot number, following state and local requirements.

Quality control swabs that are Flu A+/B− and Flu A−/B+ are provided with the kit. They should be processed in accordance with the procedure for swab specimens without transport media. If controls do not perform as expected, patient results should not be reported.

Both viable and nonviable influenza A and B viruses were detectable with the Xpect™ Flu A&B test. Due to low levels of virus shedding, inadequate specimen collection, or improper handling or transport, a negative test result does not rule out the presence of influenza virus. Consequently, the results from the Xpect™ Flu A&B test should be used in conjunction with other clinical findings to establish a diagnosis. A positive test does not rule out the possibility of co-infection with another pathogen.

In the United States, influenza is most prevalent during the winter months. During peak periods, up to 30% of specimens tested may be culture positive for influenza. The proportion of influenza A positive specimens compared to influenza B can vary dramatically from year to year, ranging from about 50% to 99%.

The performance of the Xpect™ Flu A&B test was evaluated at three sites located in the north, south and east regions of the United States. The clinical trial sites included a children's hospital (pediatric population), a university hospital (primarily adult population), and a reference laboratory (adult and pediatric (60/40) population). For all specimens evaluated, the overall sensitivity of the Xpect™ Flu A&B test when compared to culture was 92.2% ($71/77$) for influenza A and 97.8% ($45/46$) for influenza B. The overall specificity was 100% for both influenza A ($314/314$) and influenza B ($345/345$). For influenza A, there were six samples that were culture positive and Xpect™ Flu A&B negative. For influenza B, there was one sample that was culture positive and Xpect™ Flu A&B negative. Four of five discrepant samples available for analysis were positive by reverse transcription PCR (RT-PCR).

Nasal Wash (n=239)
Influenza A
92.5% Sensitivity ($37/40$); 95% CI=79.6-98.4%
100% Specificity ($199/199$); 95% CI=98.2-100%
Influenza B
100% Sensitivity ($36/36$); 95% CI=90.3-100%
100% Specificity ($203/203$); 95% CI=98.2-100%

| OVERALL | | Culture Results | | |
|---|---|---|---|---|
| | | A+/B− | A−/B+ | A−/B− |
| Xpect™ Flu A&B Results | A+/B− | 37 | 0 | 0 |
| | A−/B+ | 0 | 36 | 0 |
| | A−/B− | 3* | 0 | 163 |

*RT-PCR was performed on the three discrepant results. One of the three specimens was negative by PCR, two were positive.

Test performance by individual site:

FLU A

| | Sensitivity | | | Specificity | | |
|---|---|---|---|---|---|---|
| Site | # | % | 95% CI | # | % | 95% CI |
| 1 | 0/0 | NA | NA | 1/1 | 100 | NA |
| 2 | 3/5 | 60.0 | 14.7-94.7 | 69/69 | 100 | 94.8-100 |
| 3 | 34/35 | 97.1 | 85.1-99.9 | 129/129 | 100 | 97.2-100 |

FLU B

| | Sensitivity | | | Specificity | | |
|---|---|---|---|---|---|---|
| Site | # | % | 95% CI | # | % | 95% CI |
| 1 | 0/0 | NA | NA | 1/1 | 100 | NA |
| 2 | 0/0 | NA | NA | 74/74 | 100 | 95.1-100 |
| 3 | 36/36 | 100 | 90.3-100 | 128/128 | 100 | 97.2-100 |

Throat Swab (n=30)
Influenza A
100% Sensitivity ($^{10}/_{10}$); 95% CI=69.2-100%
100% Specificity ($^{20}/_{20}$); 95% CI=83.2-100%
Influenza B
100% Sensitivity ($^{4}/_{4}$); 95% CK=39.8-100%
100% Specificity ($^{26}/_{26}$); 95% CI=86.8-100%

| | | Culture Results | | |
|---|---|---|---|---|
| | OVERALL | A+/B− | A−/B+ | A−/B− |
| Xpect™ Flu | A+/B− | 10 | 0 | 0 |
| A&B Results | A−/B+ | 0 | 4 | 0 |
| | A−/B− | 0 | 0 | 16 |

Test performance by individual site:

FLU A

| | Sensitivity | | | Specificity | | |
|---|---|---|---|---|---|---|
| Site | # | % | 95% CI | # | % | 95% CI |
| 1 | 10/10 | 100 | 66.2-100 | 18/18 | 100 | 81.5-100 |
| 2 | 0/0 | NA | NA | 2/2 | 100 | 15.8-100 |
| 3 | NA | NA | NA | NA | NA | NA |

FLU B

| | Sensitivity | | | Specificity | | |
|---|---|---|---|---|---|---|
| Site | # | % | 95% CI | # | % | 95% CI |
| 1 | 4/4 | 100 | 39.8-100 | 24/24 | 100 | 81.5-100 |
| 2 | 0/0 | NA | NA | 2/2 | 100 | 15.8-100 |
| 3 | NA | NA | NA | NA | NA | NA |

Nasal Swab (n=122)
Influenza A
88.9% Sensitivity ($^{24}/_{27}$); 95% CI=70.8-97.7%
100% Specificity ($^{95}/_{95}$); 95% CI=96.2-100%
Influenza B
83.3% Sensitivity ($^{5}/_{6}$); 95% CI=35.9-99.6%
100% Specificity ($^{116}/_{116}$); 95% CI=96.9-100%

| | | Culture Results | | |
|---|---|---|---|---|
| | OVERALL | A+/B− | A−/B+ | A−/B− |
| Xpect™ Flu | A+/B− | 24 | 0 | 0 |
| A&B Results | A−/B+ | 0 | 5 | 0 |
| | A−/B− | 3* | 1* | 89 |

*RT-PCR was performed on two of the four discrepant specimens that were available (one influenza A and one influenza B). Both specimens were positive by PCR.

Test Performance by Individual Site:

FLU A

| | Sensitivity | | | Specificity | | |
|---|---|---|---|---|---|---|
| Site | # | % | 95% CI | # | % | 95% CI |
| 1 | 24/27 | 88.9 | 70.8-97.7 | 91/91 | 100 | 96.0-100 |
| 2 | 0/0 | NA | NA | 4/4 | 100 | 39.8-100 |
| 3 | NA | NA | NA | NA | NA | NA |

FLU B

| | Sensitivity | | | Specificity | | |
|---|---|---|---|---|---|---|
| Site | # | % | 95% CI | # | % | 95% CI |
| 1 | 5/6 | 83.3 | 35.9-99.6 | 112/112 | 100 | 96.8-100 |
| 2 | 0/0 | NA | NA | 4/4 | 100 | 39.8-100 |
| 3 | NA | NA | NA | NA | NA | NA |

The analytical sensitivity was evaluated using twelve influenza strains; six influenza A and six influenza B. Each viral strain was quantitated by $CEID_{50}$ determinations and titrated until a positive endpoint was reached using the Xpect™ Flu A&B test. The amount of virus at the endpoint dilution, expressed as $CEID_{50}$ per test, was calculated as a measure of analytical sensitivity.

| Influenza Strain | Type | Detection Limit $CEID_{50}$ |
|---|---|---|
| A/Puerto Rico/8/34 (H1N1) | A | $8.9 \times 10^3$ |
| A/Fort Monmouth/I/47 (H1N1) | A | $7.9 \times 10^1$ |
| A/New Jersey/8/76 (H1N1) | A | $8.9 \times 10^1$ |
| A/Hong Kong/8/68 (H3N2) | A | $2.8 \times 10^1$ |
| A/Victoria/3/75 (H3N2) | A | $8.9 \times 10^2$ |
| A/Port Chalmers/1/73 (H3N2) | A | $4.0 \times 10^1$ |
| B/Lee/40 | B | $7.9 \times 10^3$ |
| B/Allen/45 | B | 4 |
| B/Maryland/1/59 | B | 6 |
| B/GL/1739/54 | B | $8.9 \times 10^1$ |
| B/Taiwan/2/62 | B | 3 |
| B/Hong Kong/5/72 | B | $1.58 \times 10^2$ |

Thirty-six microorganisms were evaluated with the Xpect™ Flu A&B test. No cross-reactivity was observed for influenza A or influenza B. Bacteria and yeast isolates were tested at $10^8$ colony-forming units per ml concentration. Viral isolates were tested at concentrations of $10^4$ to $10^5$ $TCID_5$ (tissue culture infectious dose) per ml concentration. The following organisms were tested in the Xpect™ Flu A&B test.

*Acinetobacter baumannii, Bordetella pertussis, Candida albicans, Enterococcus faecalis, Escherichia coli, Gardnerella vaginalis, Haemophilus influenzae, Klebsiella pneumoniae, Lactobacillus casei, Legionella pneumophila, Listeria monocytogenes, Moraxella catarrhalis, Neisseria gonorrhoeae, Neisseria meningitidis, Neisseria sicca, Neisseria subflava, Proteus vulgaris, Pseudomonas aeruginosa, Serralia marcescens, Staphylococcus aureus* (Cowan), *Staphylococcus epidermidis, Streptococcus mutans, Streptococcus pneumoniae, Streptococcus pyogenes* Group A, *Streptococcus* Group B, *Streptococcus* Group C, *Streptococcus* Group F, Adenovirus Type 5, Coronavirus, Coxsackievirus B5, Cytomegalovirus, Parainfuenza (Sendai) Type 1, Parainfluenza Type 2, Parainfluenza Type 3, Respiratory Syncytial Virus A, Rhinovirus Type 14.

The following substances were tested with the Xpect™ Flu A&B test and no interference was observed in the assay for any substance tested at the indicated levels: whole blood (2%), three mouthwashes (25%), three throat drops (25%), three nasal sprays (25%), 4-acetomidophenol (acetaminophen) (10 mg/ml), acetylsalicylic acid (20 mg/ml), chlorpheniramine (5 mg/ml), dextromethorphan (10 mg/ml), diphenhydramine (5 mg/ml), guaiacol glyceryl ether (guaifenesin) (20 mg/ml), oxymetazoline (10 mg/ml), phenylephrine (25 mg/ml), phenylpropanolamine (20 mg/ml).

Reproducibility testing was conducted at four sites, including one in-house site, on four separate days with six blinded samples. The liquid samples consisted of diluted influenza A and influenza B antigens intended to read weakly positive or negative with the Xpect™ Flu A&B test. Ninety-nine percent of the 96 samples tested produced the expected result.

Example 7

Cazacu et al. (*J. Clinical Microbiology*, 42:3661-3664, 2004) report results of specificity and sensitivity testing of one embodiment of the invention directed to the detection of influenza A and B antigens as compared to results obtained from viral culture. Overall, the observed specificity was 100% for influenza A and B antigens in all specimen types tested, while sensitivity was 100% in throat swabs, 96.1% in nasal washes and 87.9% in nasopharyngeal swabs.

The test results obtained with the rapid lateral-flow chromatographic membrane immunoassay (Xpect™ Flu A&B, Remel Inc., Lenexa Kans.) were compared to those with the reference standard of viral culture in 400 respiratory specimens collected from children and adults who presented between January and April 2003 with respiratory or flu-like symptoms to one of three hospitals in three geographically distinct areas: Texas Children's Hospital, Houston, Tex. (n=166), University of South Florida Affiliated Hospitals and DSI Reference Laboratory, Fort Myers, Fla. (n=151), and SUNY Upstate Medical University Affiliated Hospitals, New York, N.Y. (n=83). Most (239 of 400, or 59.75%) specimens were nasal washes, 122 of 400 (30.5%) were nasopharyngeal swabs, 30 of 400 (7.5%) were throat swabs, 4 of 400 (1%) were tracheal aspirates, 3 of 400 (0.75%) were sputum, and 2 of 400 (0.5%) were obtained by bronchioalveolar lavage. Both fresh samples and samples cryopreserved for less than three months were analyzed at each institution.

Virology technicians or technologists at all centers received instruction on the test procedures and were required to pass (>90%) a blinded proficiency test on six coded samples, administered daily for four days, prior to starting testing on clinical samples included in this study. Rapid tests were performed according to the manufacturer's instructions during weekday, day shift hours. Briefly, the test detected influenza virus antigen in a test device that contained a sample well in wicking communication to reading wells that contained separate membrane strips for influenza A and influenza B viruses (FIG. 4). Each sample was mixed with a specimen diluent that contained buffered saline, detergent, a mucolytic agent, and preservative. Then, 0.20 ml was transferred by pipette into the middle of the test well of the device. A positive test was indicated by two black bands in the reading well, one in the test (T) region and one in the control (C) region. A negative test was indicated by only one black band in the C region. The absence of any black bands in the T or C regions represented an invalid test. Test readings were performed and recorded after 15 and 30 min incubation. Quality control procedures were performed and recorded for each test run or 24-h period and included both FluA+/FluB− and FluA−/FluB+ controls provided by the test kit, as well as in-house positive and negative controls for each virus. All specimens were also inoculated that same day into cell culture monolayers of human foreskin fibroblast, human lung carcinoma (A549), human epithelial (HEp2), and rhesus monkey kidney (RhMK) cells and examined daily for cytopathic effect using light microscopy. Hemadsorption with a 0.4% suspension of guinea pig red blood cells was performed on days 2, 5, and 14 of incubation of RhMK cell cultures. Virus identification was confirmed by an immunofluorescence assay with type-specific antibodies. At one institution (Texas Children's Hospital), all picornviruses were discriminated by acid lability testing to distinguish between rhinoviruses and enteroviruses. Samples with discrepant results between viral culture and the rapid influenza virus test were cryopreserved and analyzed by RT-PCR using primers able to detect and differentiate influenza A and B viruses.

Viral cultures positive for influenza virus, type A or B, were considered true positives. Sensitivity, specificity, and positive and negative predictive values were calculated using two-by-two contingency tables. Differences between tests were analyzed using Fisher's exact test. Because rapid testing for influenza virus may be performed to screen persons during a pandemic or other event affecting large numbers of people, confidence intervals (CI) for proportions were calculated, to estimate with 95% confidence, the intervals that contain the sensitivity, specificity, and predictive values for the general population, estimated in this analysis to be 1,000,000. Using the confidence intervals, results from the sample size of 400 were generalized to a large population, and the estimation predicted the interval that contained the rapid assay's performance.

The importance of this test performance is relevant in view of concerns about global pandemics of influenza, severe acute respiratory syndrome-associated coronavirus, and the possibility of a biological warfare event, indicating a need to screen large numbers of persons with febrile respiratory illness of undetermined etiology.

Of 400 specimens, 207 (51.75%) had a negative viral culture and 193 (48.25%) grew at least one virus, as shown in Table 1.

TABLE 1

Viruses isolated from respiratory samples collected from three participating centers during the 2003 influenza season

| Virus isolated | No. (%) of each virus isolated |
| --- | --- |
| Influenza A virus | 79 (40.1) |
| Influenza B virus | 46 (23.4) |
| Respiratory Syncytial Virus | 25 (12.7) |
| Parainfluenza virus | 12 (6.1) |
| Adenovirus | 8 (4.1) |
| Picornavirus | 7 (3.6) |
| Rhinovirus | 7 (3.6) |
| Enterovirus | 4 (2.0) |
| Cytomegalovirus | 7 (3.6) |
| Herpes Simplex Virus | 2 (1.0) |
| Total no. of viruses isolated | 197* |

*Four samples had dual viral infections, as described in the text.

Dual viral infections were detected in four specimens (one with influenza A virus and adenovirus, one with influenza A virus and respiratory syncytial virus, one with influenza B virus and cytomegalovirus, and one with picornavirus and adenovirus), to give a total of 197 viruses isolated during the study period. The mean duration that elapsed until viral cultures were detected as positive was 4.43±2.87 days, and 87.6% of cultures were positive with seven days.

The overall sensitivity of the rapid test to detect both types of influenza virus was slightly higher (95.2% versus 94.4%) at the 30-min reading than the 15-min reading, but specificity and predictive values were essentially the same at both readings. No significant differences were observed in the ability of the test to detect influenza A or B virus, and the results were generalized with 95% confidence to a population of at least 1,000,000, as shown in Table 2.

TABLE 2

Performance of the lateral-flow chromatographic membrane immunoassay (RA), at 15- and 30-min readings, compared to that of viral culture (CX) for detection of influenza A and B viruses[a]

| RA | RA+ and CX+ | RA+ and CX− | RA− and CX+ | RA− and CX− | Sensitivity (CI) | Specificity (CI) | PVP (CI) | PVN (CI) |
|---|---|---|---|---|---|---|---|---|
| At 15 min | | | | | | | | |
| Both A and B | 118 | 0 | 7 | 275 | 94.4 (92.1-96.6) | 100 (98.8-100) | 100 (98.8-100) | 97.5 (95.9-99) |
| A only | 73 | 0 | 6 | 321 | 92.4 (89.8-95) | 100 (98.8-100) | 100 (98.8-100) | 98.2 (96.8-99.5) |
| B only | 45 | 0 | 1 | 354 | 97.8 (96.4-99.2) | 100 (98.8-100) | 100 (98.8-100) | 99.7 (98.7-100) |
| At 30 min | | | | | | | | |
| Both A and B | 119 | 0 | 6 | 275 | 95.2 (93.1-97.3) | 100 (98.8-100) | 100 (98.8-100) | 97.9 (96.4-99.3) |
| A only | 74 | 0 | 5 | 321 | 93.7 (91.2-96.1) | 100 (98.8-100) | 100 (98.8-100) | 98.5 (97.2-99.7) |
| B only | 45 | 0 | 1 | 354 | 97.8 (96.4-99.2) | 100 (98.8-100) | 100 (98.8-100) | 99.7 (98.7-100) |

[a]CI, 95% confidence interval results generalized to population of 1 million; PVP, predictive value positive; PVN, predictive value negative; A, influenza type A virus; B, influenza type B virus.

No significant differences were found when performance statistics were analyzed by center site.

No false-positive tests were observed at either the 15- or 30-min incubation time for the rapid test. There were seven false-negative results at 15 min, and six false-negative results at the 30-min incubation time. Only nasal washes (three) and nasopharyngeal swabs (three) had false-negative results. Overall, the specificity of the rapid assay was 100% for all specimen types. Sensitivity was 100% in throat swabs, 96.1% in nasal washes, and 87.9% in nasopharyngeal swabs.

False-negative results were detected at all three centers, and testing by RT-PCR of the five specimens with apparent discrepant results confirmed four of the false-negative test results, as shown in Table 3.

| Specimen no. | Site[a] | Specimen[b] | Influenza virus type | Days to CX+[c] | RA[d] at: 15 min | 30 min | RT-PCR |
|---|---|---|---|---|---|---|---|
| 16 | DSI | NP | A | 3 | − | − | A+ |
| 41 | DSI | NP | A | 3 | − | Weak+ | NT[e] |
| 77 | DSI | NP | A | 2 | − | − | NT[f] |
| 163 | UMU | NW | A | 3 | − | − | A+ |
| 171 | UMU | NW | A[g] | 3 | − | − | A−/B−[g] |
| 361 | TCH | NW | A | 5 | − | − | A+ |
| 118 | DSI | NP | B | 3 | − | − | B+ |

[a]DSI, DSI Laboratories; UMU, Upstate Medical University; TCH, Texas Children's Hospital.
[b]NP, Nasopharyngeal swab; NW, nasal wash.
[c]CX, culture in RhMK cell monolayer.
[d]RA, rapid assay.
[e]NT, not tested, RT-PCR was not performed on this specimen because the lateral-flow assay was positive at 30 min.
[f]Not tested, RT-PCR was not performed because the quantity of specimen available was insufficient.
[g]Repeat RA was also negative. Respiratory syncytial virus was also detected on day 4 in Hep-2 monolayer cell culture. The possibility of a cross-contamination of cell tubes, causing a false-positive cell culture result for influenza A virus, cannot be excluded as a possible cause of discrepant results with sample 171.

The immunoassay was both highly sensitive and specific in detecting and differentiating influenza A and B viruses in respiratory specimens collected from patients in three different geographic locations during a recent influenza season in the United States. The results were favorable when statistically generalized to a larger population, making the assay useful for screening large numbers of individuals. Many previous studies on the performance of rapid assays for detecting influenza virus were limited because they were conducted at a single center or during an influenza season where only type A predominated. In addition, in the few studies in which influenza B virus circulated, significant rates of false-negative tests have been observed. Dual infections with one type of influenza virus and another virus were observed in this study, providing a reminder that a positive rapid test for influenza A or B virus does not eliminate the possibility that the patient may be coinfected with another virus that may be contributing to their symptoms.

The current availability of at least seven different test kits for the rapid detection of influenza virus in clinical samples not only enhances individual patient care, but also may help control the spread of influenza if infected individuals are accurately diagnosed and treated promptly and if outbreaks are identified early and controlled by timely immunization practices. However, healthcare workers caring directly for patients, as well as laboratory directors and public health officials, should be aware of the performance characteristics, availability, cost, and reimbursement issues associated with each rapid test and choose the best one for their specific needs and, once implemented, monitor the performance of the test in their particular setting.

In addition to the above examples, other target analytes, including antigens indicative of infectious disease, hormones, antibodies, receptors, and the like, present suitable analytes for detection using dextran-polystreptavidin conjugates as capture reagents in conjunction with appropriate biotinylated and labeled conjugates to detect target analytes with suitable specificity and sensitivity.

All cited publications or references are expressly incorporated by reference herein in their entirety.

Other variations or embodiments of the invention will also be apparent to one skilled in the art from the above description, figures, and examples. Thus, the foregoing embodiments are not to be construed as limiting the scope of the invention.

What is claimed is:

1. A solid phase immunoassay device comprising:
   a first porous carrier comprising a nitrocellulose test strip with dextran-polystreptavidin polymer immobilized directly thereto at a test site,
   a second porous carrier upstream of and in wicking flow communication with the first porous carrier, the second porous carrier comprising a sample receiving area and a conjugate site, the conjugate site comprising a mobilizable biotinylated antibody and a labeled antibody,
   wherein each of said mobilizable biotinylated antibody and labeled antibody is capable of specifically binding a target antigen when present within said sample.

2. The device of claim 1 further comprising a backing layer.

3. The device of claim 1 further comprising an absorbent pad downstream of said test site and optional control site.

4. The device of claim 1 in a single housing.

5. The device of claim 1 wherein the second porous carrier material is selected from the group consisting of porous plastic or glass fiber.

6. The device of claim 1 wherein said target antigen is an antigen indicative of the presence of influenza A in the sample.

7. The device of claim 1 wherein said target antigen is an antigen indicative of the presence of influenza B in the sample.

8. The device of claim 1 wherein the labeled antibody is labeled with a detectable particle.

* * * * *